(12) United States Patent
Rezach

(10) Patent No.: US 11,849,979 B1
(45) Date of Patent: Dec. 26, 2023

(54) SPINAL IMPLANT SYSTEM AND METHOD

(71) Applicant: Warsaw Orthopedic, Inc., Warsaw, IN (US)

(72) Inventor: William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/744,937

(22) Filed: May 16, 2022

(51) Int. Cl.
*A61B 17/70* (2006.01)
*A61B 17/86* (2006.01)

(52) U.S. Cl.
CPC ...... *A61B 17/7041* (2013.01); *A61B 17/7032* (2013.01); *A61B 17/8665* (2013.01); *A61B 17/8685* (2013.01); *A61B 17/8695* (2013.01)

(58) Field of Classification Search
CPC ............ A61B 17/7041; A61B 17/7032; A61B 17/8665; A61B 17/8685; A61B 17/8695
USPC ....... 606/268, 264, 265, 266, 267, 269, 270, 606/271, 272, 277, 278, 301, 305, 308, 606/310, 319, 320
See application file for complete search history.

(56) References Cited

U.S. PATENT DOCUMENTS

| | | | |
|---|---|---|---|
| 5,536,268 A | 7/1996 | Griss | |
| 5,643,263 A * | 7/1997 | Simonson | A61B 17/7038 606/279 |
| 6,309,391 B1 | 10/2001 | Crandall et al. | |
| 7,322,979 B2 | 1/2008 | Crandall et al. | |
| 7,678,112 B2 | 3/2010 | Rezach | |
| 8,430,917 B2 | 4/2013 | Rezach | |
| 9,622,788 B2 | 4/2017 | Rezach et al. | |
| 2002/0173789 A1 * | 11/2002 | Howland | A61B 17/7038 606/279 |
| 2003/0105460 A1 * | 6/2003 | Crandall | A61B 17/7041 606/279 |
| 2006/0241596 A1 * | 10/2006 | Rezach | A61B 17/7035 606/301 |
| 2007/0123860 A1 * | 5/2007 | Francis | A61B 17/7049 606/250 |
| 2010/0030274 A1 * | 2/2010 | Mitchell | A61B 17/7046 606/264 |
| 2012/0296380 A1 * | 11/2012 | Simonson | A61B 17/7038 606/279 |
| 2018/0049777 A1 * | 2/2018 | Rezach | A61B 17/7082 |
| 2018/0228518 A1 * | 8/2018 | Carruth | A61B 17/7001 |
| 2021/0153907 A1 * | 5/2021 | Armstrong | A61B 17/7049 |

* cited by examiner

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A spinal construct includes a bone fastener including a post and a shaft portion engageable with vertebral tissue. The post being movable in one or more axes relative to the shaft portion. A receiver defines a first cavity configured for disposal of the bone fastener and a second open cavity configured for disposal of a spinal rod. A band is disposable in the first cavity. The band being contractible and defining an inner surface that is directly engageable with the post. A nut includes an inner surface being slidably engageable over the post and an end surface engageable with the band such that the band contracts to engage the post. Systems, surgical instruments, implants and methods are disclosed.

19 Claims, 14 Drawing Sheets

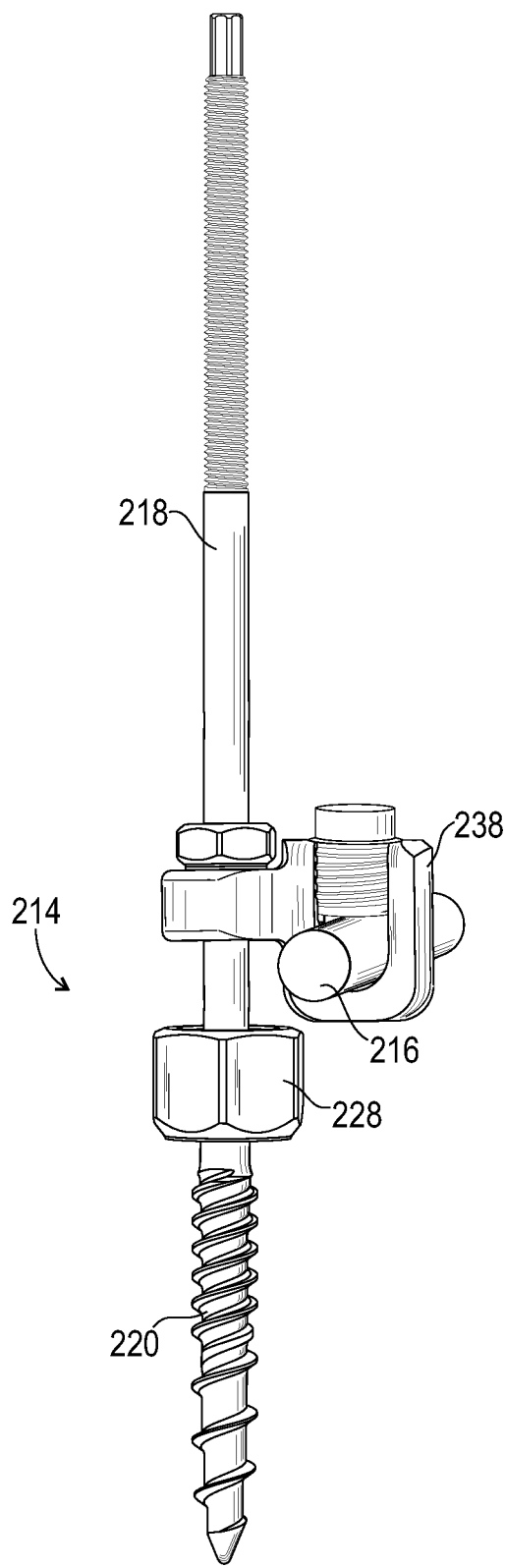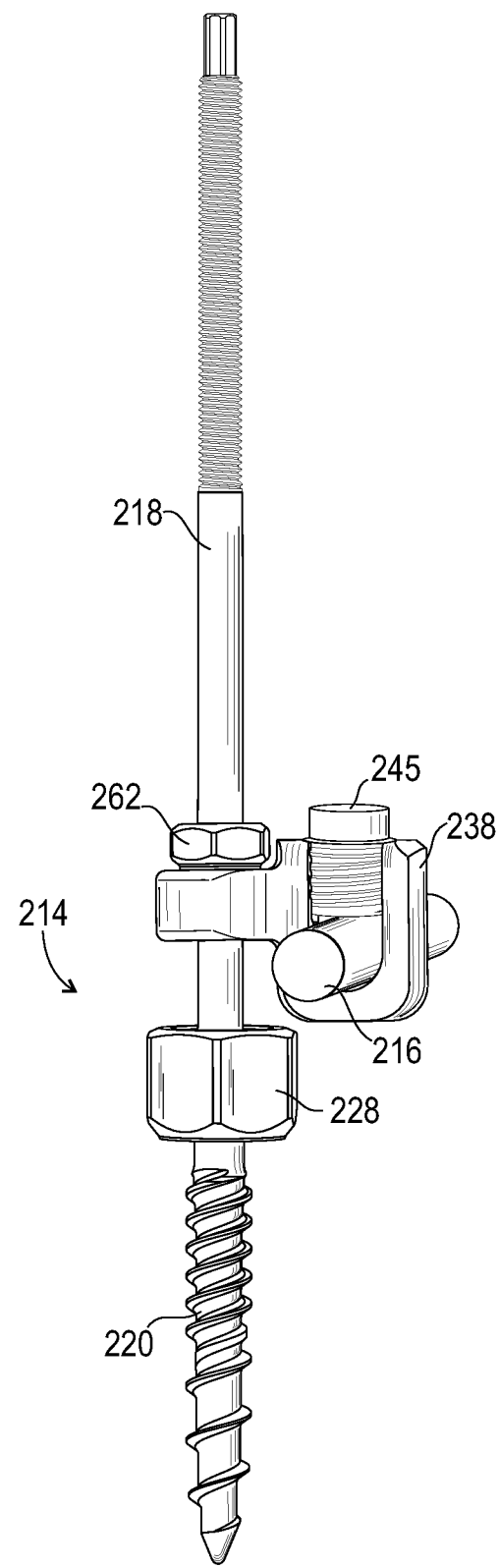
FIG. 22  FIG. 23

US 11,849,979 B1

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct includes a bone fastener including a post and a shaft portion engageable with vertebral tissue. The post being movable in one or more axes relative to the shaft portion. A receiver defines a first cavity configured for disposal of the bone fastener and a second open cavity configured for disposal of a spinal rod. A band is disposable in the first cavity. The band being contractible and defining an inner surface that is directly engageable with the post. A nut includes an inner surface being slidably engageable over the post and an end surface engageable with the band such that the band contracts to engage the post. In some embodiments, systems, surgical instruments, implants and methods are disclosed.

In one embodiment, the spinal construct includes a multi-planar adjusting screw including a post and a shaft portion engageable with vertebral tissue. A receiver defines a first cavity configured for disposal of the multiplanar adjusting screw and a top loading cavity configured for disposal of a spinal rod. A collet is disposable in the first cavity. The collet defining an inner surface that is directly engageable with the post. A nut includes an inner surface being engageable with the post and an end surface engageable with the collet between a first orientation such that the inner surfaces are substantially aligned and a second orientation such that the collet is movable to fix the post with the receiver.

In one embodiment, a spinal implant system is provided. The spinal implant system includes an adjustable bone fastener including a post connected with a threaded shaft via a joint. A receiver defines a first cavity configured for disposal of the bone fastener and a second open cavity. A band is disposable in the first cavity. The band is contractible and defines an inner surface that is directly engageable with the post. A nut includes an inner surface being engageable with the post and an end surface engageable with the band such that the band contracts to fix the post with the receiver. A spinal rod is disposable in the second cavity.

BRIEF DESCRIPTION OF THE DRAWINGS

The present disclosure will become more readily apparent from the specific description accompanied by the following drawings, in which.

and

Figure 12:
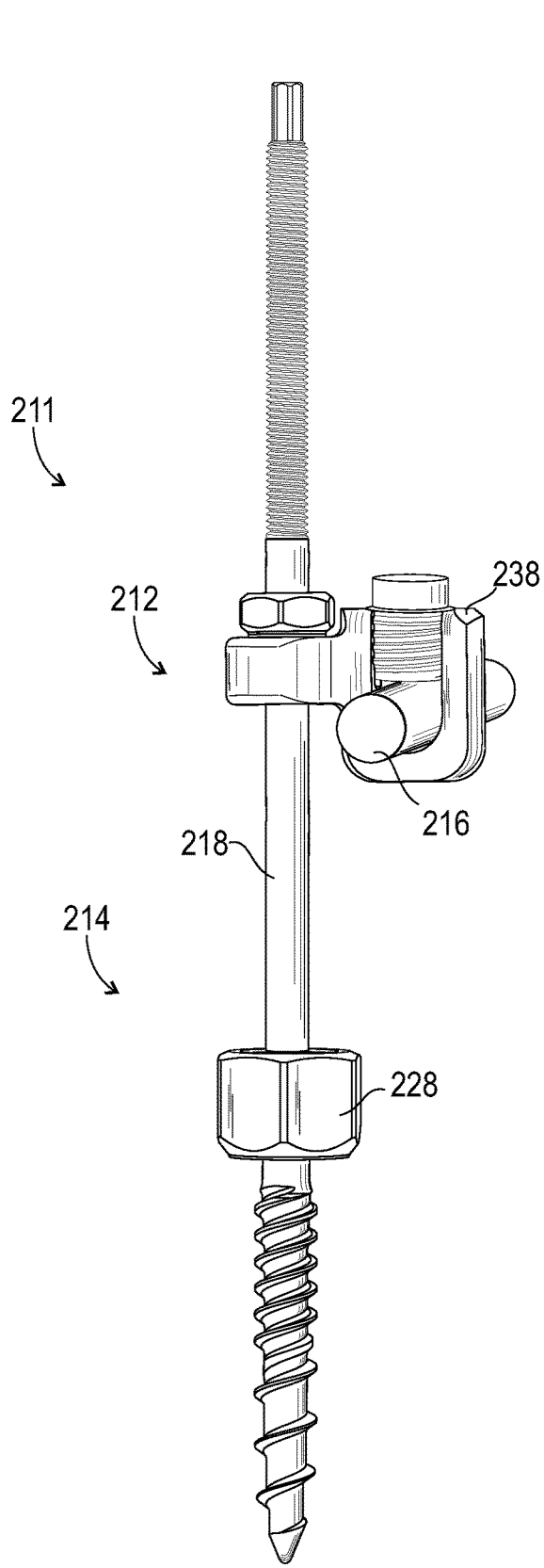
FIG. 12 is a perspective view of components of one embodiment of a system in accordance with the principles of the present disclosure.
Figure 18:
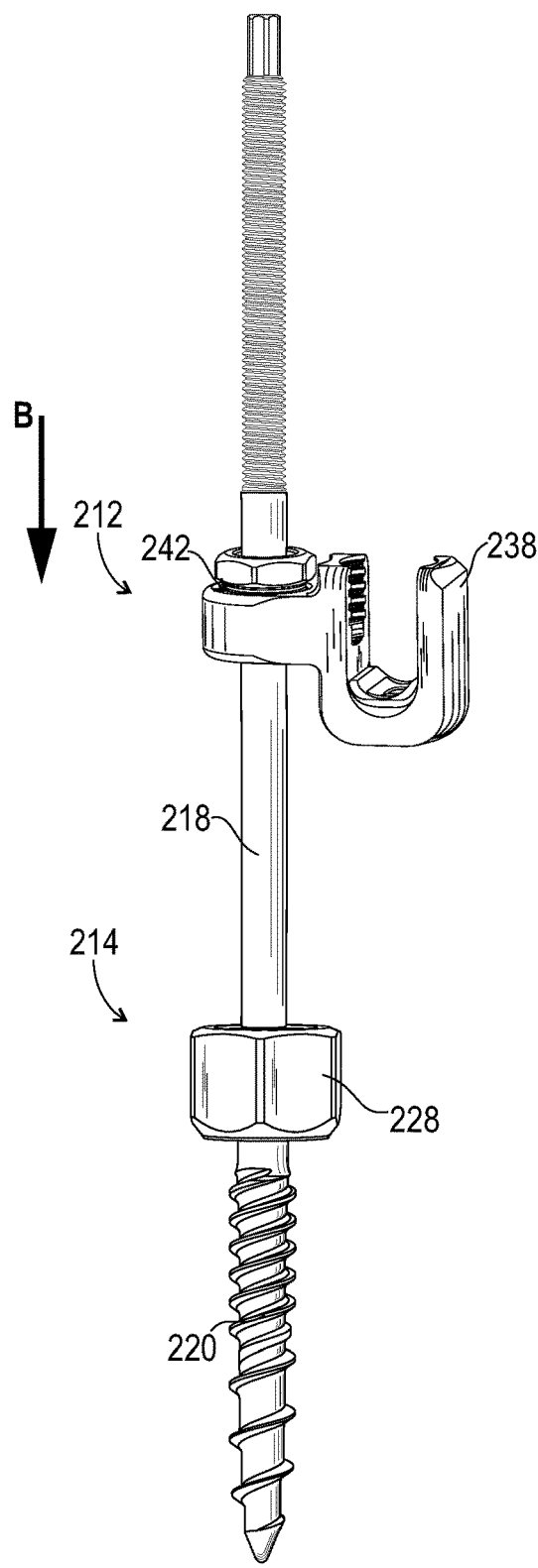
Figure 19:
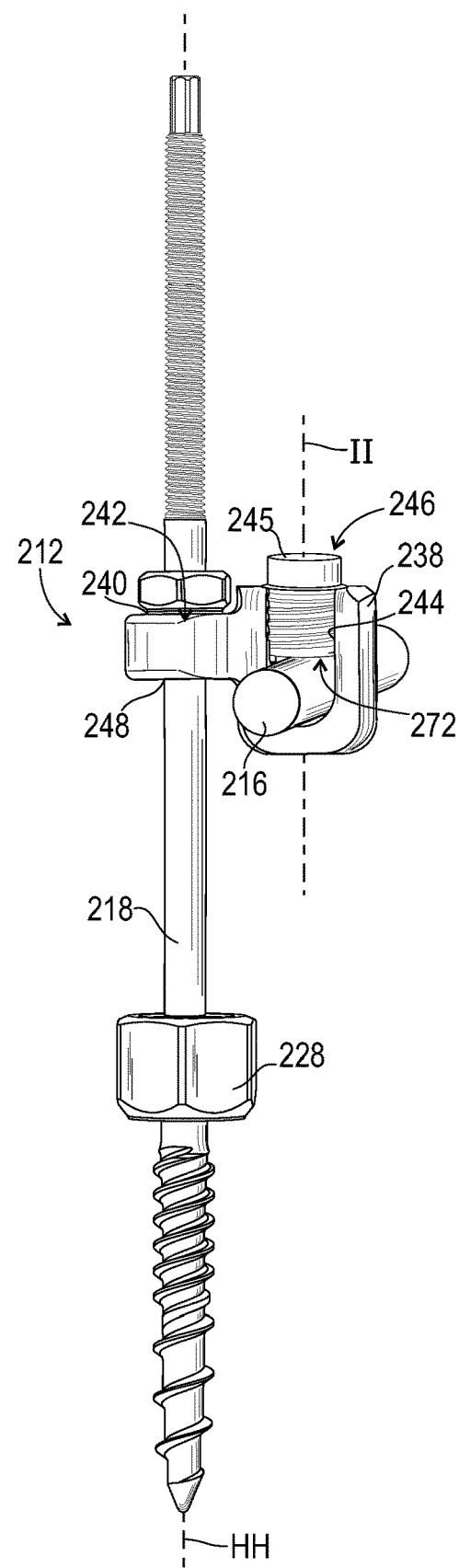
Figure 20:
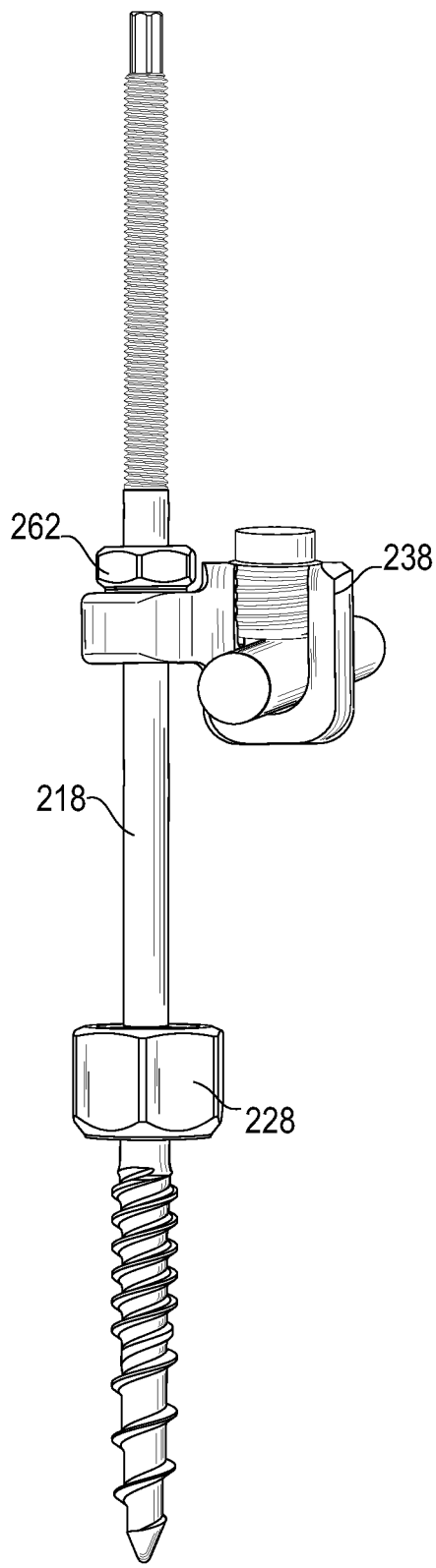
Figure 21:
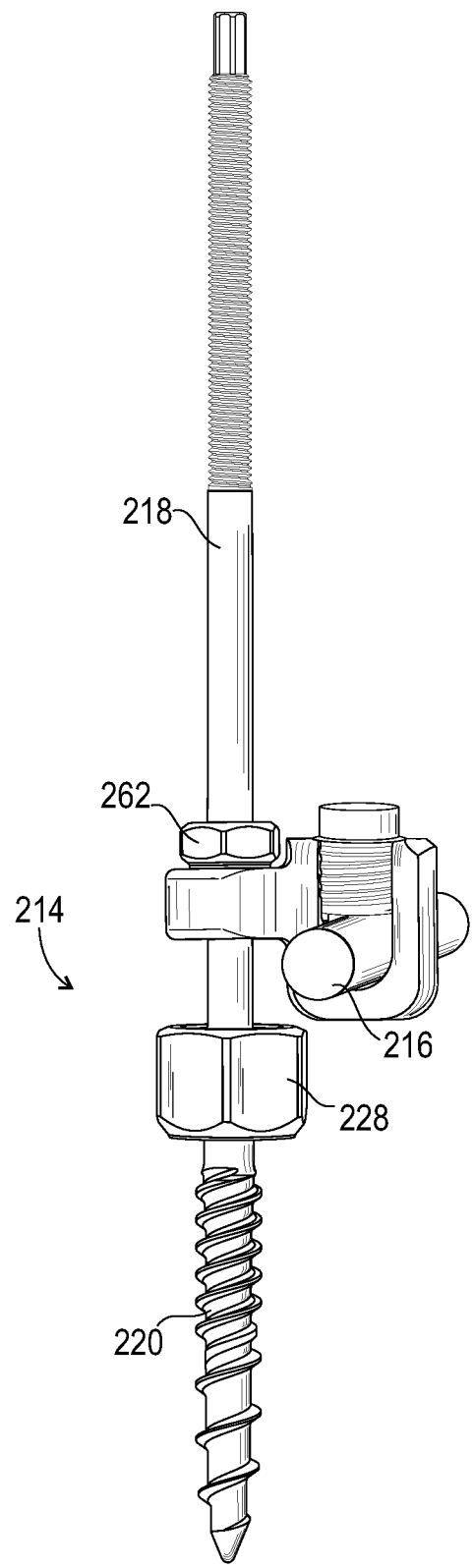

FIG. 18 is a perspective view of components shown in FIG. 12;

FIG. 19 is a perspective view of the components shown in FIG. 12;

FIG. 20 is a perspective view of the components shown in FIG. 12;

FIG. 21 is a perspective view of the components shown in FIG. 12;

FIG. 22 is a perspective view of the components shown in FIG. 12;

FIG. 23 is a perspective view of the components shown in FIG. 12.

DETAILED DESCRIPTION

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the present surgical system includes a spinal construct having one or more components that facilitate spatial adjustment of the spinal construct relative to vertebral tissue and/or components of the spinal construct implanted with vertebral tissue. In some embodiments, the spinal construct includes one or more components configured for height adjustment in a dorsal orientation relative to a bone screw fixed with vertebral tissue. In some embodiments, the spinal construct is adjusted without fully reducing a spinal rod with one or more receivers of the spinal construct. In some embodiments, the spinal construct includes one or more components that can be adjusted in orientations, for example, medial, lateral, sagittal, coronal, transverse, relative to vertebral tissue and/or components of the spinal construct implanted with vertebral tissue. In some embodiments, the systems and methods of the present disclosure are employed with a spinal joint fusion, for example, with a cervical, thoracic, lumbar and/or sacral region of a spine.

In some embodiments, the present surgical system includes a spinal construct comprising a connector. In some embodiments, the connector is configured for engagement with a spinal implant, for example, a top loading bone screw and a spinal implant, for example, a spinal rod. In some embodiments, a height of the connector is configured for adjustment in an orientation, for example, a dorsal orientation relative to the screw. In some embodiments, the connector is adjusted without fully reducing the spinal rod to a preset position to lock the spinal construct. In some embodiments, the connector is configured to accommodate procedures performed on a plane of a body and/or vertebrae, for example, a sagittal plane. In some embodiments, the connector is configured for use in deformity correction procedures including spondylolisthesis, kyphosis and scoliosis correction procedures.

In some embodiments, the present surgical system includes a connector configured to facilitate top loading of a screw with the connector and dorsal height forgiveness of the connector relative to the screw. In some embodiments, the screw includes a multi-axial screw, a multi-planar adjusting screw, and/or a uni-axial screw. In some embodiments, the connector is configured to clamp or lock onto a post of the screw. In some embodiments, the connector is configured to facilitate reduction of a spinal rod relative to a vertebral surface of a patient, for example vertebrae. In some embodiments, the connector is configured to suspend reduction of the spinal rod at any time during a procedure. In some embodiments, nerve monitoring and/or tactile feedback can be implemented during the procedure to determine whether to discontinue the application of a reduction force to the spinal rod.

In some embodiments, the present surgical system includes a connector, including a receiver. In some embodiments, the surgical system includes a band, for example, a collet. In some embodiments, the collet includes a split ring collet. In some embodiments, the collet is configured for disposal in a first cavity of the receiver and is configured for engagement with a post of a spinal implant, for example, a bone screw. In some embodiments, the surgical system includes a nut. In some embodiments the nut is configured for disposal in the first cavity and is configured for engagement with the collet. In some embodiments, the nut includes concave ends. In some embodiments, the receiver includes a second cavity. In some embodiments, the second cavity is transverse relative to the first cavity. In some embodiments, the second cavity is configured for engagement with a spinal implant, for example, a spinal rod. In some embodiments, the surgical system includes a saddle and a threaded pin. In some embodiments, the threaded pin is configured to retain the saddle within the second cavity. In some embodiments, the threaded pin includes a press fit pin or a laser welded pin. In some embodiments, the connector is configured for disposal about a multi-planar adjusting screw joint.

In some embodiments, the present connector includes a medial-lateral profile. In some embodiments, the multi-planar adjusting screw joint is positioned in a medial/lateral orientation. In some embodiments, the connector includes a low profile height. In some embodiments, the connector is configured to accommodate procedures performed on the sagittal plane of a body and/or vertebrae. In some embodiments, the saddle is configured for +/−20 degrees of translation to accommodate the sagittal plane during rod reduction to selectively align the rod.

In some embodiments, the present surgical system includes a connector having a locking mechanism including a band, for example, a collet and a nut. In some embodiments, the collet includes an exterior surface that defines one or more flats that are configured to mate with one or more flats defined from an interior surface of a cavity of the receiver. In some embodiments, the exterior surface defines one or more threads and the nut includes an interior surface that defines one or more threads. In some embodiments, the collet and the nut are configured for threaded engagement. In some embodiments, the one or more flats are configured to prevent rotation of the collet as the nut threadingly engages with the collet. In some embodiments, the nut includes one or more chamfers configured for mating engagement with one or more chamfers on the post.

In some embodiments, the present surgical system includes a connector having a receiver configured for engagement with a bone screw and a spinal rod. In some embodiments, the bone screw includes a multi-axial screw. In some embodiments, the bone screw includes a shank and a head. In some embodiments, the head is configured for engagement with a post and a base. In some embodiments, the post is configured for modular connection with the bone screw. In some embodiments, modular connection includes a pop-on connection. In some embodiments, an end of the post is welded onto an inner surface of the base superior to a resilient member, for example, an upper ring. In some embodiments, the end of the post is spot welded onto the inner surface of the base. In some embodiments, a 2-5 Newton-Meter (Nm) breaking torque is applied to the post to break the weld such that the post can translate within the base to engage the head of the bone screw. In some embodiments, the post is configured for locked engagement with the bone screw. In some embodiments, the post includes a threaded end that translates within the base.

In some embodiments, the post of the present surgical system is translated within the body and the threads are fully threaded with an inner threaded surface of the base. In some embodiments, multi-axial rotation occurs when the threads are fully threaded within the base. In some embodiments, a portion of the thread is not disposed within the base to display that the post is in a non-locked orientation. In some embodiments, a surgical instrument, for example, a counter torque driver is employed to prevent the base from rotating on the shank. In some embodiments, the post is configured for disposal with a first cavity of the connector and is moved in a downward direction toward the base and the bone screw. In some embodiments, the spinal rod is configured for disposal with a second cavity of the receiver to secure the spinal rod with the connector. In some embodiments, the spinal rod is provisionally secured with a set screw. In some embodiments, the spinal rod is provisionally secured with the setscrew and can slide through a spinal implant. In some embodiments, the spinal rod is reduced along the post. In some embodiments, spinal rod reduction can be stopped at any location. In some embodiments, the base includes a multi-axial joint. In some embodiments, the multi-axial joint is locked relative to the bone screw. In some embodiments, the multi-axial joint is locked via a torque limit handle. In some embodiments, a surgical instrument, for example, a counter torque driver and/or a crow-foot device is implemented to prevent the base from rotating during locking. In some embodiments, a nut disposed with the first cavity of the receiver and the setscrew are tightened to fix the rod with the first cavity. In some embodiments, a user breaks off the post from the base and the head.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-9, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, spinal implant system 10 is configured for use in deformity correction procedures including spondylolisthesis, kyphosis and scoliosis correction procedures. In some embodiments, one or more of the components of spinal implant system 10 are configured for engagement with existing spinal constructs, which may include fastener implants and/or spinal rod implants attached with vertebrae, in a revision surgery to manipulate tissue and/or correct a spinal disorder, as described herein.

Figure 1:
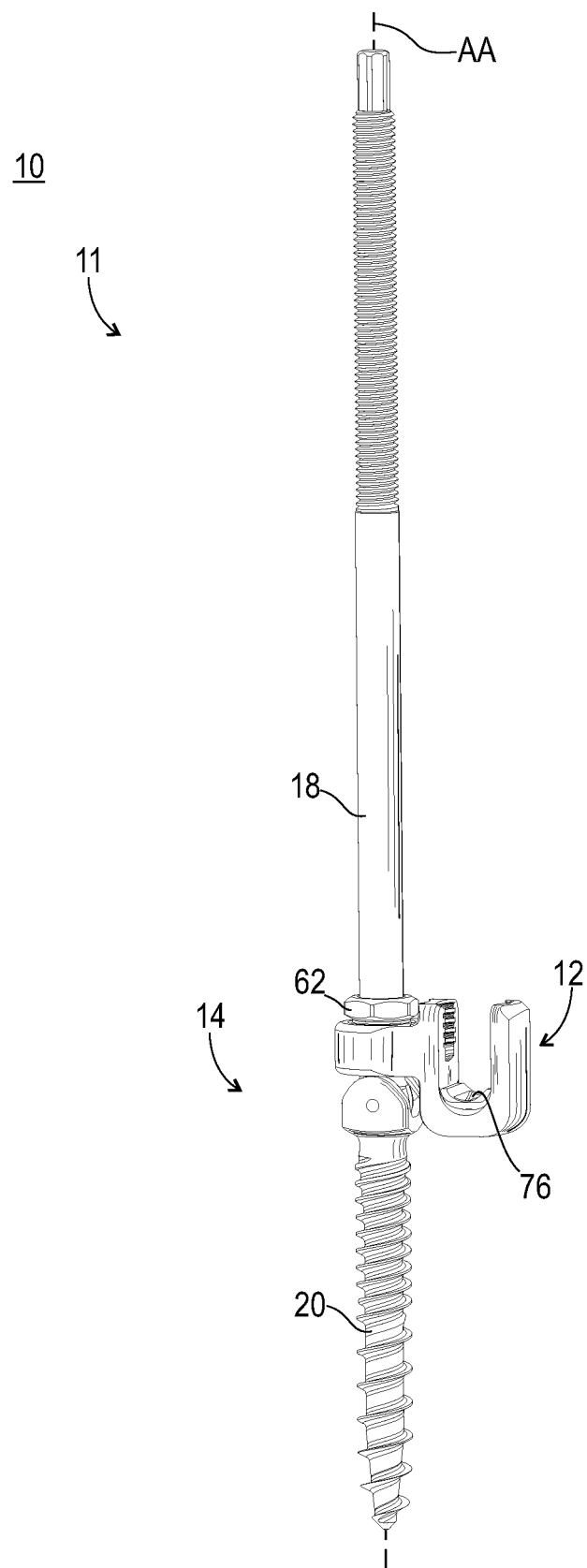
FIG. 1 is a perspective view of components of one embodiment of a spinal implant system in accordance with the principles of the present disclosure.
Figure 5:
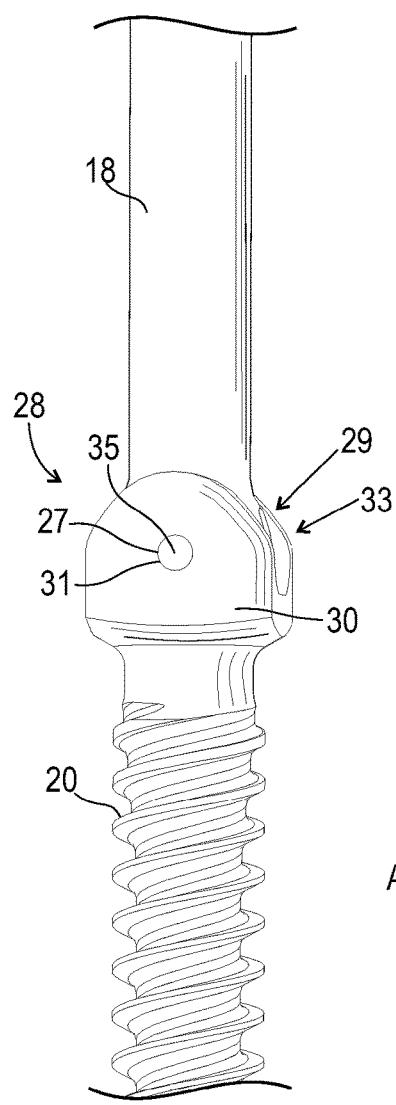
FIG. 5 is an enlarged perspective view of components shown in FIG. 1.
Figure 8:
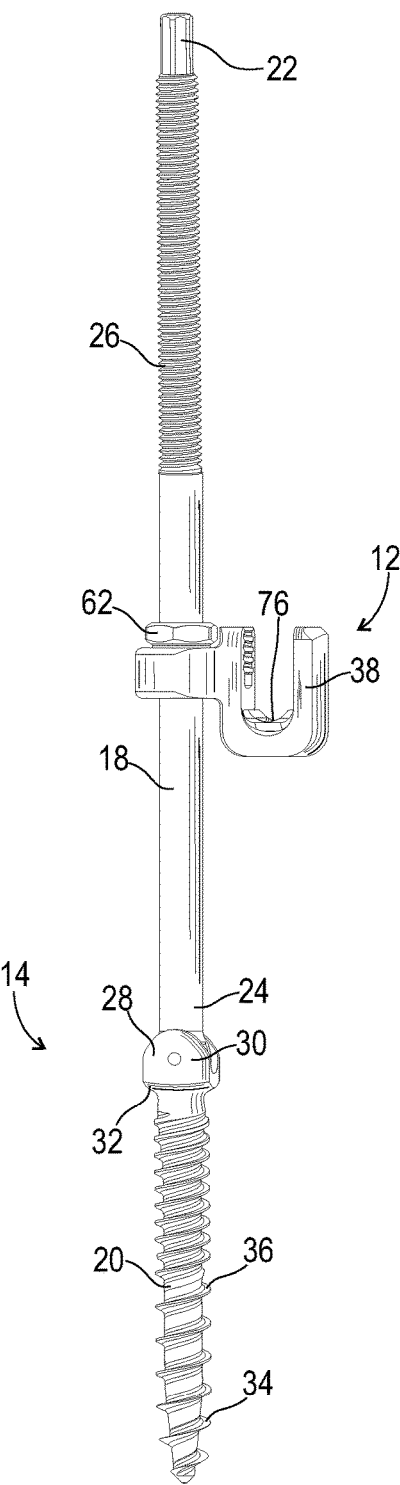
FIG. 8 is a perspective view of the components shown in FIG. 1.

Spinal implant system 10 comprises a spinal construct 11 including a connector 12 and a bone fastener, for example, a multi-planar adjusting screw 14, as shown in FIG. 1. Connector 12 is configured for dorsal height adjustment relative to a post 18 of screw 14, as shown in FIG. 1 and described herein. Screw 14 extends along a longitudinal axis AA, as shown in FIG. 1. Screw 14 includes post 18 connected to a threaded shaft 20, as shown in FIGS. 1 and 5. Post 18 is movable to one or a plurality of axes relative to shaft 20 and longitudinal axis AA. Post 18 includes an end 22 and an end 24, as shown in FIG. 8. End 22 engages with one or more instruments, for example, a driver (not shown) to rotate screw 14. End 22 includes threads 26. In some embodiments, all or one or more portions of end 22 is smooth, rough, arcuate, undulating, mesh, porous, semi-porous, dimpled and/or textured. In some embodiments, all or one or more portions of end 22 can fracture and separate at a predetermined force or torque limit from end 24. In some embodiments, all or one or more portions of end 22 includes one or more deformable elements, for example, a tab, wire, projection, tang, rim, and/or bar to facilitate fracture and separation. In some embodiments, end 22 may be fabricated from a homogenous material or heterogeneously fabricated from different materials, and/or alternately formed of a material having a greater degree, characteristic or attribute of plastic deformability, frangible property and/or break away quality to facilitate fracture and separation from end 24. In some embodiments, end 22 is fabricated from a frangible material, including a rubber, adhesive, metal and/or a plastic. In some embodiments, end 22 disengages from end 24 via a surgical instrument, for example, a cutting device (not shown).

End 24 includes a joint 28 connected to a head 30 of shaft 20, as shown in FIG. 5. Joint 28 is configured to enable post 18 to move and/or rotate through one plane relative to shaft 20 and/or longitudinal axis AA. In some embodiments, joint 28 is configured as a mono-axial, bi-axial, multi-axial, fixed, spheroidal or cylindrical joint to facilitate movement and/or rotation of post 18 as described herein. In some embodiments, joint 28 is oriented in a medial lateral direction relative to screw 14. In some embodiments, joint 28 is oriented in a selected direction, including sagittal, coronal, transverse, dorsal, medial, and/or lateral relative to screw 14. Joint 28 is formed from a portion of head 30 and a portion of end 22, as shown in FIG. 5. End 24 includes openings 27, 29 and head 30 includes openings 31, 33. A pin 35 is disposed with openings 27, 29 and 31, 33. In some embodiments, joint 28 is a single monolithic piece formed from end 22 and engages a surface of head 30 in a modular and/or pop-on engagement. In some embodiments, post 18 disengages with shaft 20 at joint 28. In some embodiments, post 18 disengages from shaft 20 when a torque limit is applied to post 18.

Shaft 20 engages with vertebral tissue. Shaft 20 extends from an end 32 to an end 34, as show in FIG. 8. End 32 includes head 30 and end 34 includes a threaded portion 36. In some embodiments, threaded portion 36 may include a single thread turn or a plurality of discrete threads. In some embodiments, all or portions of end 34 is smooth, rough, arcuate, undulating, mesh, porous, semi-porous, dimpled and/or textured. In some embodiments, the bone fastener may include sagittal angulation screws, pedicle screws, multi-axial screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

Figure 2:
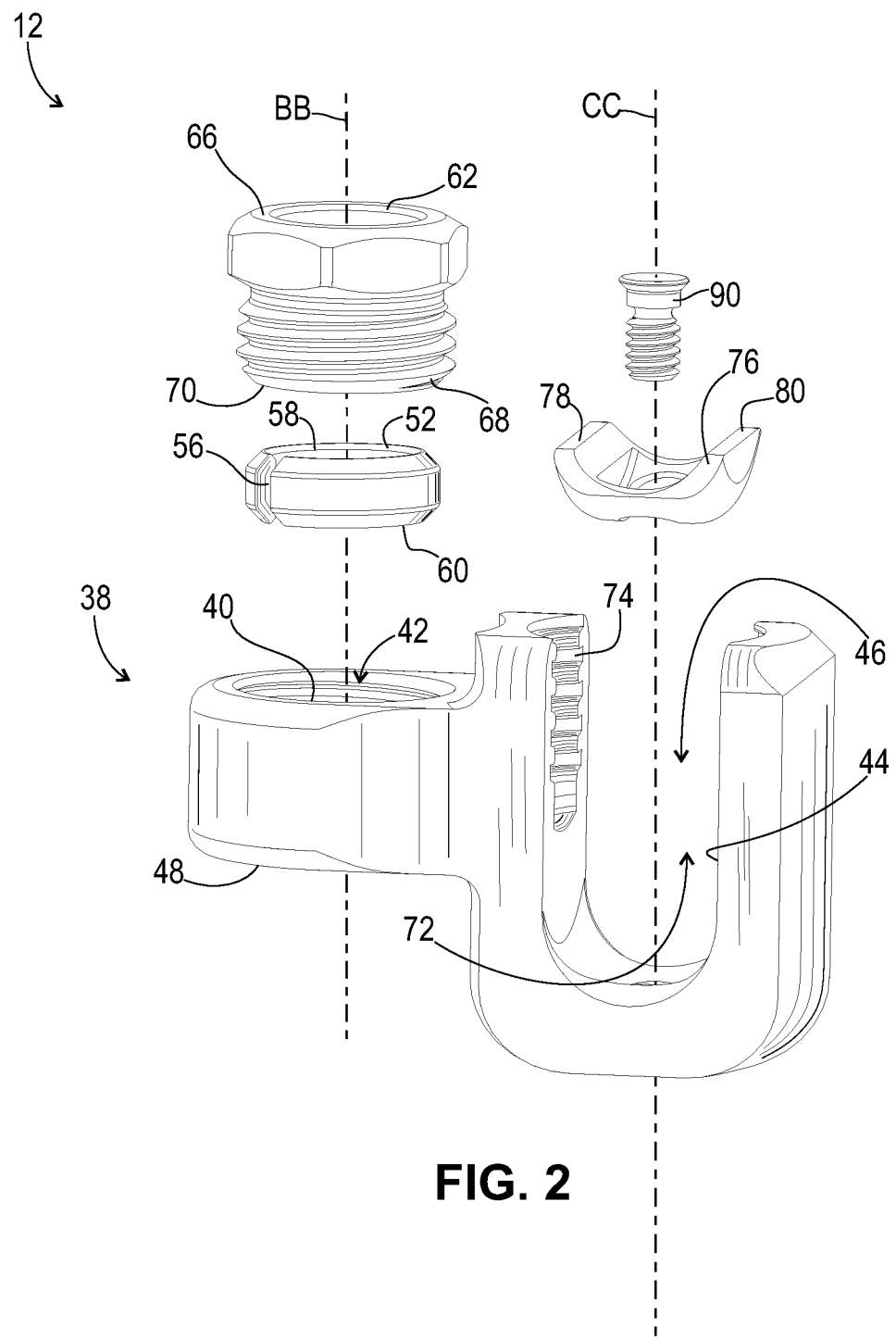
FIG. 2 is a perspective view of components shown in FIG. 1 with parts separated.
Figure 4:
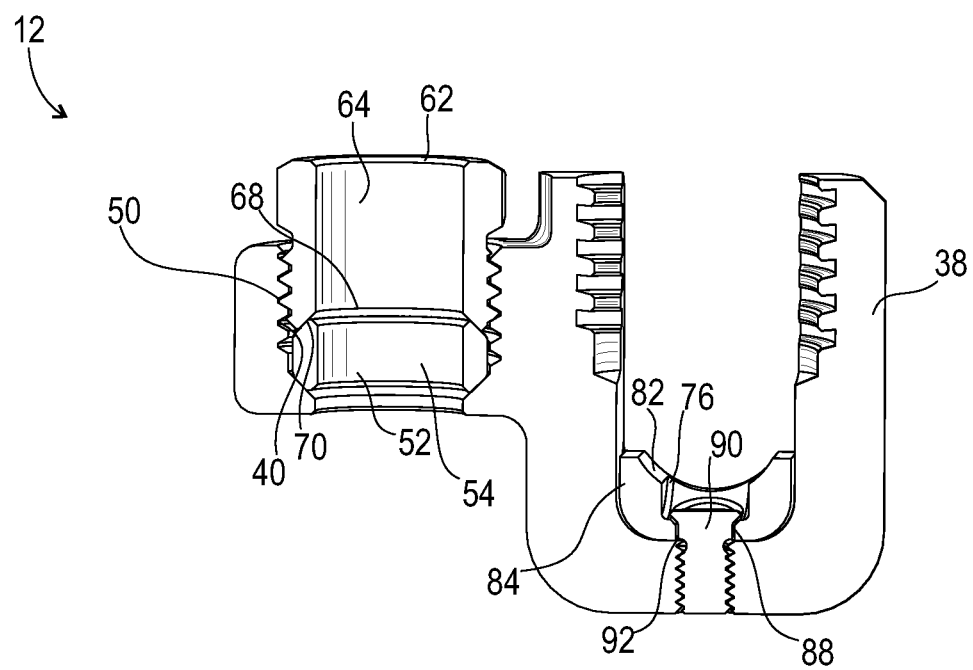
FIG. 4 is a cross section view of the components shown in FIG. 3.
Figure 9:
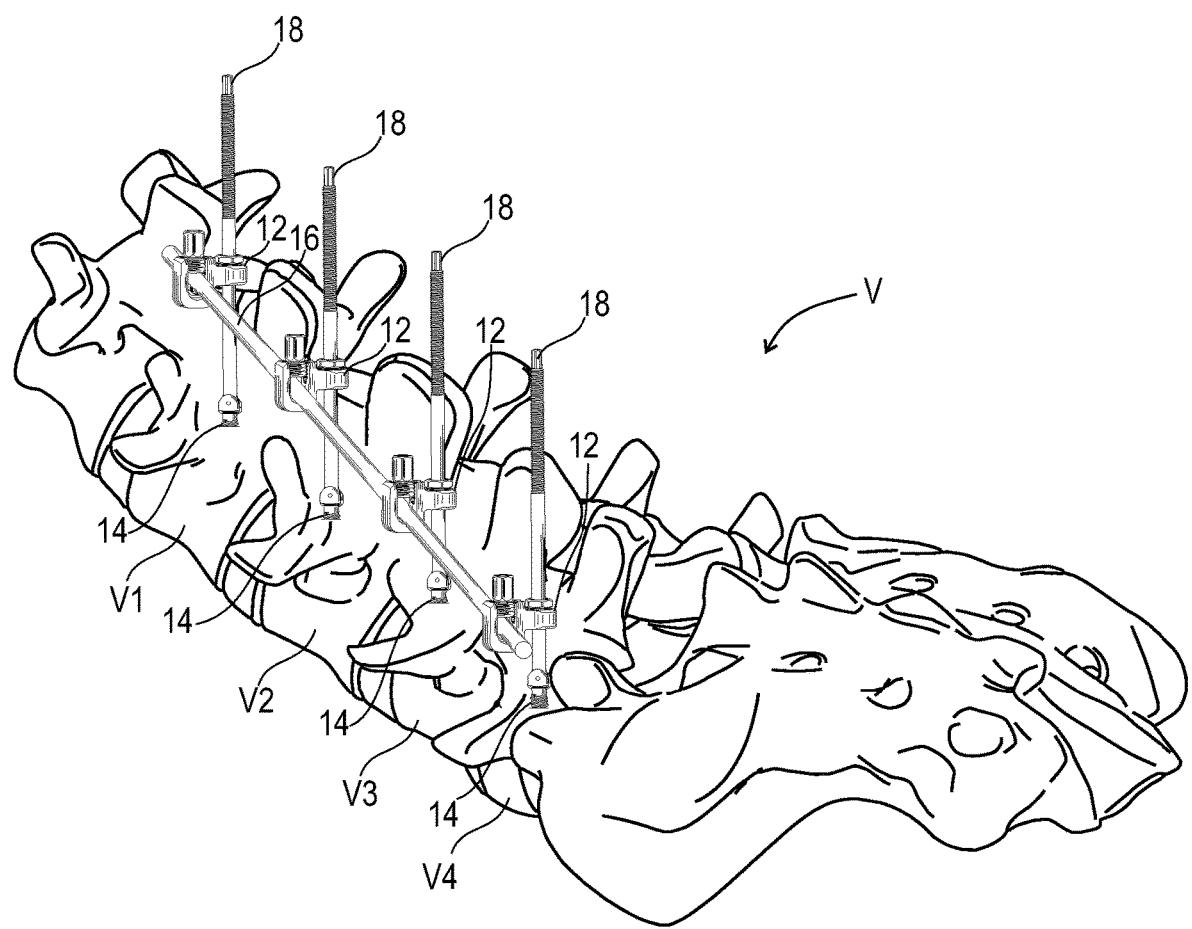
FIG. 9 is a perspective view of components of one embodiment of a spinal implant system in accordance with the principles of the present disclosure disposed with vertebrae.

Connector 12 is configured to facilitate procedures performed on a body and/or vertebrae of a patient in a selected plane for example, a sagittal plane. Connector 12 is engageable with screw 14 and a spinal rod 16, as shown in FIG. 9. In some embodiments, connector 12 is configured for adjustment in a selected plane, including sagittal, coronal, transverse, dorsal and/or medial/lateral. Connector 12 includes a receiver 38, as shown in FIG. 2. Receiver 38 is configured for dorsal height adjustment relative to post 18. An inner surface 40 of receiver 38 defines a cavity 42 for disposal of screw 14 and an inner surface 44 of receiver 38 defines an open cavity 46 for disposal of rod 16. Cavity 42 extends along a longitudinal axis BB and includes a longitudinal passageway 48. Surface 40 defines one or more threads 50, as shown in FIG. 4. A band, such as a collet 52, for example, is disposed with cavity 42 and threads 50 facilitate inward flex of collet 52 to contract collet 52 within cavity 42, as described herein. Cavity 42 includes a substantially circular cross section. In some embodiments, cavity 42 may have various cross section configurations, for example, oval, oblong, triangular, rectangular, square, polygonal, irregular, uniform, non-uniform, variable and/or tapered. In some embodiments, all or a portion of surface 40 is smooth, rough, arcuate, undulating, mesh, porous, semi-porous, dimpled and/or textured. In some embodiments, receiver 38 is configured for sagittal, coronal, transverse, dorsal and/or medial/lateral height adjustment relative to post 18.

Collet 52 is contractible and defines an inner surface 54 that is directly engageable with post 18, as shown in FIGS.

4 and 6. In some embodiments, surface 54 is smooth, rough, arcuate, undulating, mesh, porous, semi-porous, dimpled and/or textured. Collet 52 includes a gap 56 that is adjustable to fix post 18 with receiver 38, as shown in FIG. 2. In some embodiments, gap 56 enables expansion and/or contraction of collet 52. Collet 52 extends between an end 58 and an end 60, as shown in FIG. 2. End 58 is configured for engagement with a nut 62, as described herein. Ends 58, 60 are angled. In some embodiments, all or a portion of ends 58, 60 include straight edges, are beveled, flared, and/or convex.

Figure 7:
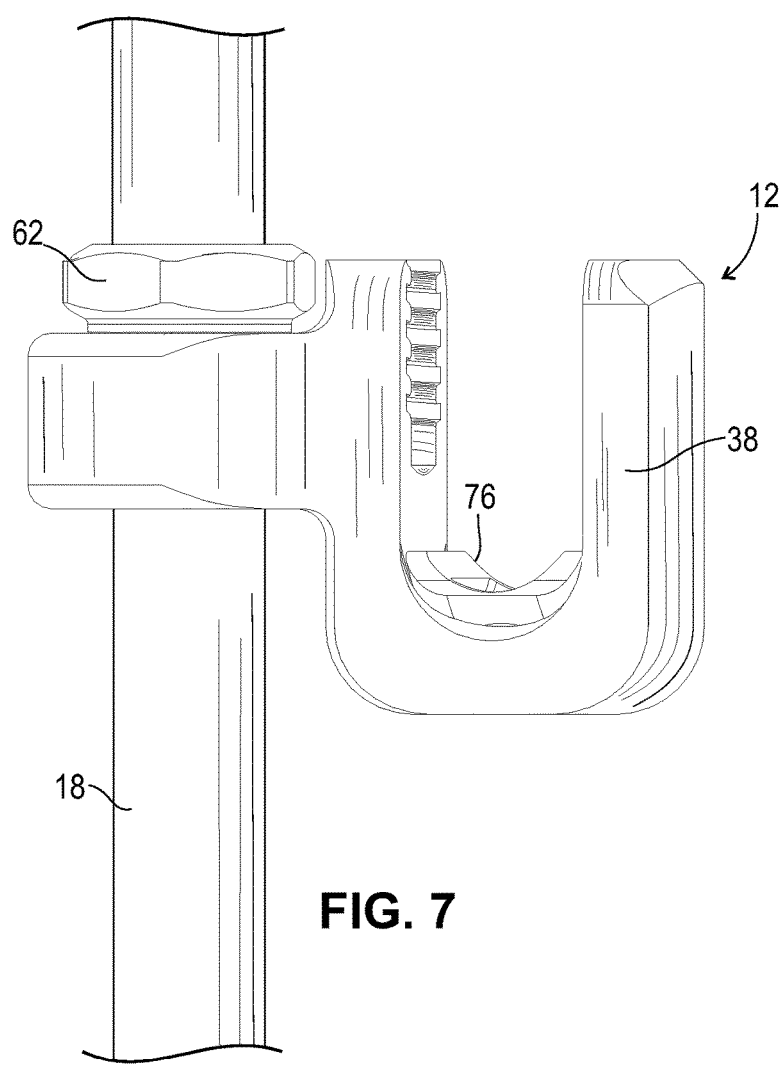
FIG. 7 is a break away view of components shown in FIG. 1.

Nut 62 is disposable in cavity 42, as shown in FIG. 2. Nut 62 includes an inner surface 64 slidable over post 18. Nut 62 extends between an end surface 66 and an end surface 68. End surface 68 engages with collet 52 such that collet 52 contracts to fix post 18 with receiver 38, as shown in FIGS. 1 and 7. End surface 68 is engageable with collet 52 between an orientation such that surfaces 54, 64 are substantially aligned, as shown in FIG. 4, and an orientation such that collet 52 is contractible to fix post 18 with receiver 38, as shown in FIG. 1. End surface 68 includes a concave surface 70, as shown in FIG. 4, disposed to abut collet 52 to drive collet 52 inward to contract collet 52. In the orientation where collet 52 is contractible to fix post 18 with receiver 38, force is applied to nut 62 by a user and/or instrument, for example, a driver (not shown) to drive collet 52 inward into cavity 42, for example, into one of threads 50, as shown in FIG. 4. In some embodiments, a portion of end surface 68 is driven inward into surface 54. In some embodiments, nut 62 is torqued in a range of 8-12 Nm to fix post 18 with receiver 38.

Cavity 46 of receiver 38 extends along a longitudinal axis CC and includes a transverse passageway 72 relative to longitudinal passageway 48, as shown in FIG. 2. Cavity 46 includes a top loading cavity configured for disposal of rod 16. Surface 44 includes a threaded portion 74 configured for engagement with threads of a setscrew (not shown). Cavity 46 includes a substantially U-shaped cross section. In some embodiments, cavity 46 may have various cross section configurations, such as, for example, circular, oval, oblong, triangular, rectangular, square, polygonal, irregular, uniform, non-uniform, variable and/or tapered. In some embodiments, all or portions of surface 44 is smooth, rough, arcuate, undulating, mesh, porous, semi-porous, dimpled and/or textured.

A saddle 76 is disposed with cavity 46, as shown in FIGS. 2 and 4. Saddle 76 translates relative to receiver 38 to accommodate movement of rod 16 supported by saddle 76 in a plane, for example, a sagittal plane of a body and/or vertebrae. Saddle 76 receives and movably supports rod 16 such that rod 16 can translate axially, rotate and/or pivot relative to receiver 38 along and about axis CC prior to fixation with saddle 76. In some embodiments, saddle 76 facilitates +/−20 degrees of translation to accommodate movement of rod 16 supported by saddle 76 in the sagittal plane.

Figure 3:
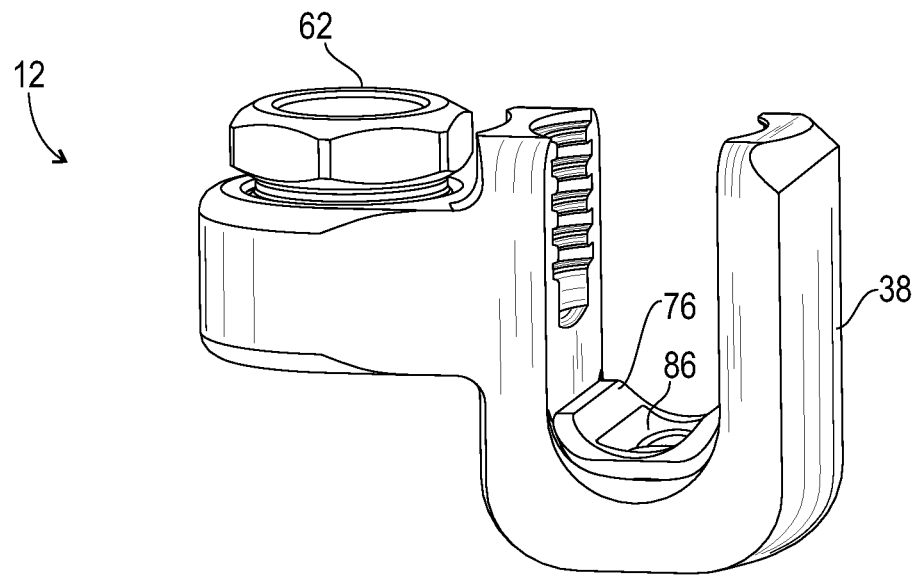
FIG. 3 is a perspective view of components shown in FIG. 1.

Saddle 76 extends between an end 78 and an end 80, as shown in FIG. 2. Saddle 76 includes an outer surface 82 that defines a wall 84, as shown in FIG. 4. Wall 84 is configured to engage surface 44. Surface 82 defines a concave portion 86, as shown in FIG. 3, that engages at least a portion of rod 16. Saddle 76 includes an opening 88 for disposal with a threaded pin 90 as shown in FIG. 4 and described herein. In some embodiments, rod 16 may be disposed within passageway 72 for relative movement in orientations relative to axis CC, such as, for example, transverse, perpendicular and/or other angular orientations such as acute or obtuse, co-axial and/or may be offset or staggered. In some embodiments, saddle 76 may be monolithically formed as a portion of receiver 38.

Pin 90 retains saddle 76 within cavity 46. Surface 44 defines an opening 92 for disposal of pin 90, as shown in FIG. 4. Pin 90 is fixed with saddle 76 and opening 92. In some embodiments, all or a portion of pin 90 is threaded. In some embodiments, all or a portion of pin 90 is rough, arcuate, undulating, mesh, porous, semi-porous, dimpled and/or textured to facilitate engagement or fixation with saddle 76 and opening 92. In some embodiments, pin 90 includes a press fit pin, a laser welded pin, or other mechanical fixture.

In some embodiments, connector 12 includes a set screw (not shown). The set screw is disposed with cavity 46 and engages with thread portion 74 of surface 44 and rod 16 to fix rod 16 with cavity 46. In some embodiments, surface 44 may be disposed with the set screw in alternate fixation configurations, such as, for example, friction fit, pressure fit, locking protrusion/recess, locking keyway and/or adhesive. In some embodiments, all or only a portion of surface 44 may have alternate surface configurations to enhance engagement with spinal rod 16 and/or the set screw such as, for example, rough, arcuate, undulating, mesh, porous, semi-porous, dimpled and/or textured. The set screw is configured for engagement with rod 16 to facilitate fixation and/or locking of rod 16 with passageway 72. The set screw is disposable with cavity 46 between a non-locking orientation, such that rod 16 is translatable relative to connector 12 and a locked orientation, such that the set screw fixes rod 16 with connector 12.

In some embodiments, spinal implant system 10 can include one or a plurality of connectors 12 such as those described herein, which may be employed with a single vertebral level or a plurality of vertebral levels. In some embodiments, one or more connectors 12 may be engaged with vertebrae in various orientations, such as, for example, series, parallel, offset, staggered and/or alternate vertebral levels. In some embodiments, one or more connectors 12 may be employed with multi-axial screws, sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, is employed with a surgical procedure, such as, for example, a surgical treatment of an applicable condition or injury of an affected section of a spinal column and adjacent areas within a body. In some embodiments, spinal implant system 10 includes spinal construct 11 including connector 12 and screw 14, as described herein. Connector 12 is configured for dorsal height adjustment relative to post 18 of screw 14, as shown in FIG. 1. In some embodiments, connector 12 is configured to facilitate procedures performed on a body and/or vertebrae of a patient on a selected plane for example, a sagittal plane. Connector 12 is configured for connection with screw 14 and spinal rod 16, as shown in FIG. 9.

In some embodiments, connector 12 can be employed for use in deformity correction procedures including spondylolisthesis, kyphosis and scoliosis correction procedures. In some embodiments, connector 12 can be employed in a surgical treatment such as a revision surgery to strengthen, revise, repair and/or extend an existing spinal construct. In some embodiments, spinal implant system 10, including spinal construct 11, is employed in a revision surgery to connect with an existing spinal construct and strengthen the existing spinal construct to span one or more spinal levels. In some embodiments, the existing spinal construct may include one or more implants connected or fixed with tissue in a prior or different surgical procedure, separate in time and/or over a duration of time in the same surgical procedure. In some embodiments, during a surgical treatment, spinal implant system 10 may be completely or partially revised, removed or replaced.

In connection with the surgical procedure, to treat a selected section of vertebrae V, as shown in FIG. 9, a medical practitioner obtains access to a surgical site including vertebrae V in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access the surgical site. The surgical pathway is utilized for implantation of components of spinal implant system 10. A preparation instrument (not shown) can be employed to prepare tissue surfaces of vertebrae V, as well as for aspiration and irrigation of a surgical region.

Figure 6:
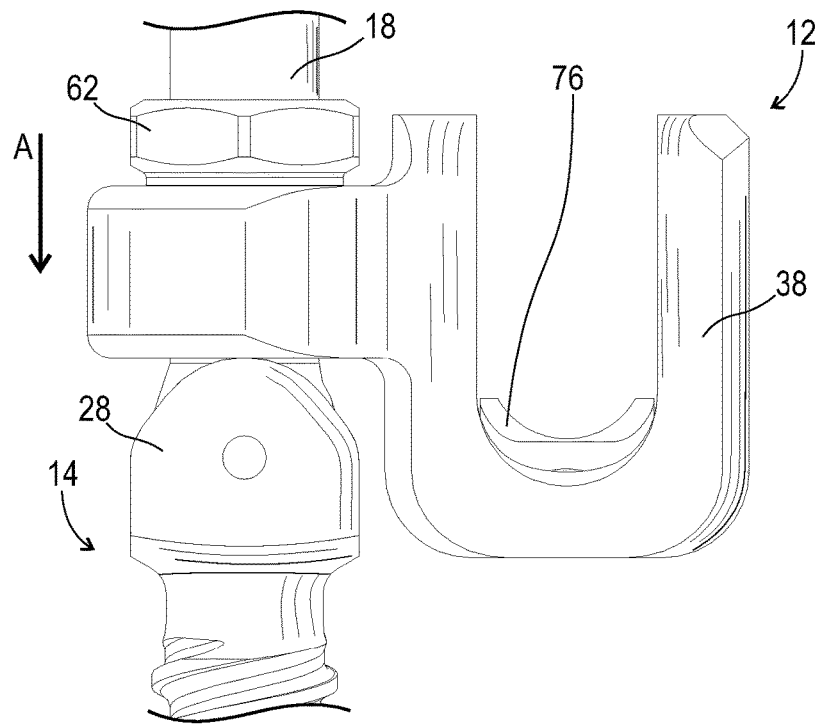
FIG. 6 is a break away view of components shown in FIG. 1.

Screw 14 is fixed with vertebral tissue via shaft 20. Collet 52 is disposed within cavity 42, as shown in FIG. 4. Connector 12 engages with screw 14 via disposal of post 18 with cavity 42, as shown in FIG. 6. Rod 16 is disposed with cavity 46. Connector 12 is translated in a direction, as shown by arrow A in FIG. 6, toward joint 28 to dorsally adjust connector 12. Nut 62 engages with post 18 and is translated in the direction shown by arrow A. End surface 68 of nut 62 is disposed with cavity 42 and abuts with end 58 of collet 52 in an orientation to substantially align inner surface 64 of nut 62 with inner surface 54 of collet 52, as shown in FIG. 4. Torque is applied to nut 62 and end surface 68 abuts end 58 to drive collet 52 inward to contract collet 52 to fix post 18 with receiver 38 positioning nut 62 in an orientation, thereby locking post 18 with receiver 38.

Rod 16 is reduced to a selected position. A setscrew (not shown) is disposed with cavity 46 and engages with threads 74. A surgical instrument, for example, a driver (not shown) is employed to drive the setscrew into cavity 46 to lock rod 16 with passageway 72. All or a portion of post 18 is removed via break away and/or a surgical instrument, for example, a cutting device (not shown) above nut 62, as described herein.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, robotics, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

Figure 10:
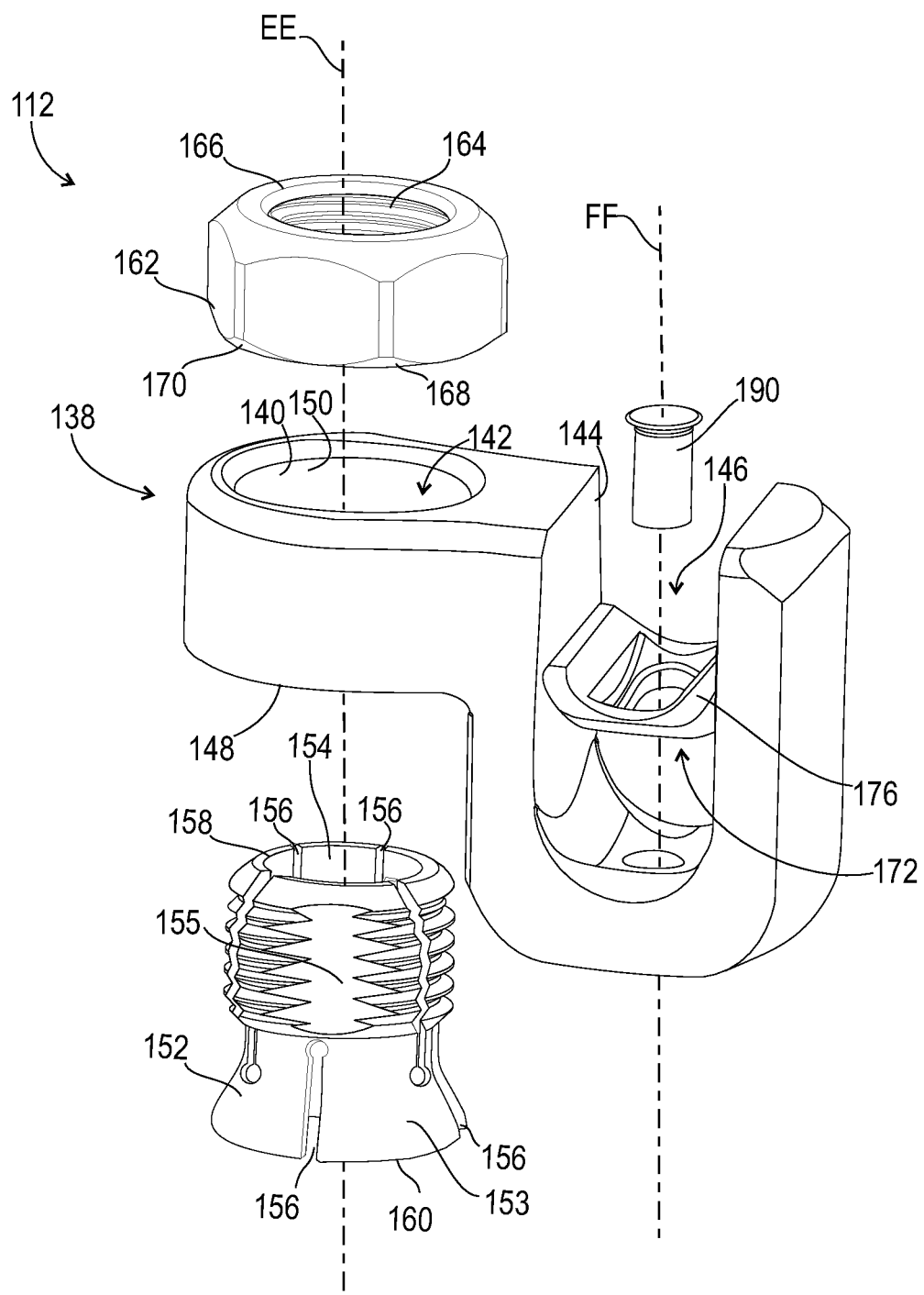
FIG. 10 is a perspective view of components of one embodiment of a spinal implant system in accordance with the principles of the present disclosure with parts separated.
Figure 11:
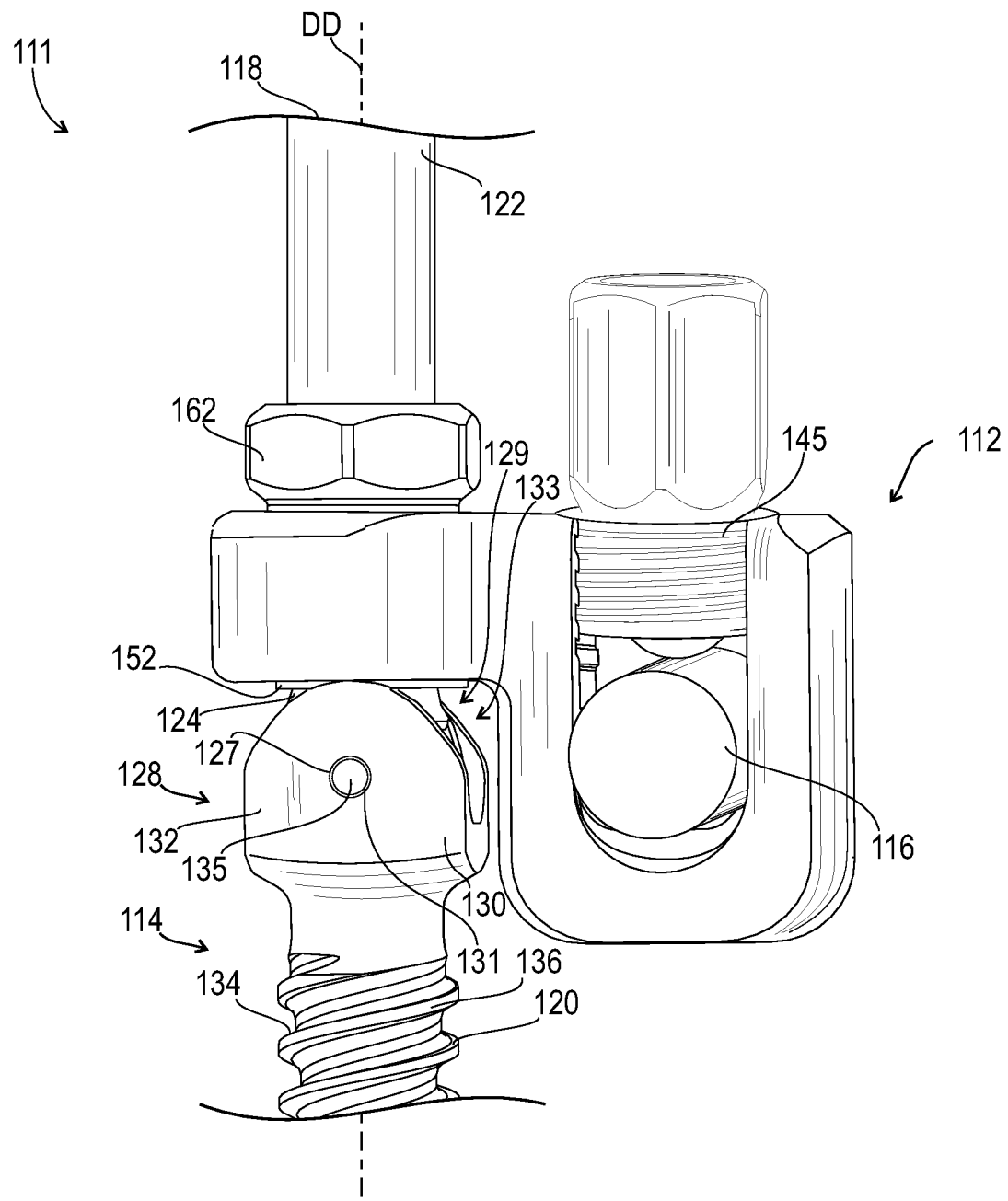
FIG. 11 is a break away view of components shown in FIG. 10.

In one embodiment, as shown in FIGS. 10 and 11, spinal implant system 10, similar to the systems and methods described herein, includes a spinal construct 111, similar to spinal construct 11. Spinal construct 111 includes a connector 112 and a bone fastener, for example, a multi-planar adjusting screw 114, as shown in FIG. 11, similar to screw 14 described herein. Connector 112 is configured for dorsal height adjustment relative to a post 118 of screw 114, as shown in FIG. 11 and described herein. Screw 114 extends along a longitudinal axis DD, as shown in FIG. 11. Screw 114 includes post 118, similar to post 18, connected to a threaded shaft 120, similar to shaft 20. Post 118 is movable in one or a plurality of axes relative to shaft 120 and longitudinal axis DD. Post 118 includes an end 122 and an end 124, as shown in FIG. 11. End 122 engages with one or more instruments, for example, a driver (not shown) to rotate screw 114.

End 124 includes a joint 128, similar to joint 28 described herein, as shown in FIG. 11. Joint 128 is connected to a head 130, similar to head 30 described herein, of shaft 120. Joint 128 is configured to enable post 118 to move and/or rotate through one plane relative to shaft 120 and/or longitudinal axis DD. In some embodiments, joint 128 is positioned in a medial lateral direction relative to screw 114. Joint 128 is formed from a portion of head 130 and a portion of end 122, as shown in FIG. 11. End 124 includes openings 127, 129 and head 130 includes openings 131, 133. A pin 135 is disposed with openings 127, 129 and 131, 133. In some embodiments, post 118 disengages from shaft 120 when a torque limit is applied to post 118.

Shaft 120, similar to shaft 20 described herein, engages with vertebral tissue. Shaft 120 extends from an end 132 to an end 134, as show in FIG. 11. End 132 includes head 130 and end 134 includes a threaded portion 136.

Connector 112 is configured to facilitate procedures performed on a body and/or vertebrae of a patient on a selected plane for example, a sagittal plane. Connector 112 is engageable with screw 114 and a spinal rod 116, as shown in FIG. 11. Connector 112 includes a receiver 138, similar to receiver 38 described herein, as shown in FIG. 10. Receiver 138 is configured for dorsal height adjustment relative to post 118. An inner surface 140 of receiver 138 defines a cavity 142, similar to cavity 42 as described herein, for disposal of screw 114 and an inner surface 144 of receiver 138 defines an open cavity 146 for disposal of rod 116. Cavity 142 extends along a longitudinal axis EE and includes a longitudinal passageway 148. Surface 140 includes one or more flats 150. In some embodiments, flats 150 may be discrete, planar portions. A band, such as a collet 152, for example, includes an outer surface 153 that defines one or more flats 155. Flats 155 are configured for disposal with cavity 142 and engagement with flats 150, as shown in FIG. 10. Engagement between flats 150, 155 prevents rotation of collet 152 when a nut 162 is in a threaded engagement with collet 152, described herein.

Collet 152 is contractible and defines an inner surface 154 that is directly engageable with post 118. Collet 152 includes gaps 156 that are adjustable to fix post 118 with receiver 138. In some embodiments, gaps 156 enable expansion and contraction of collet 152. In some embodiments, gaps 156 can be variously configured including, but not limited to, axial and/or transverse gaps. Collet 152 extends between an end 158 and an end 160. End 158 is configured for engagement with nut 162, as described herein. End 158 is angled.

Nut 162, similar to nut 62 as described herein, is adapted to engage collet 152. Nut 162 includes an inner surface 164 slidable over post 118. Nut 162 extends between an end surface 166 and an end surface 168. End surface 168 is configured for engagement with receiver 138 such that collet 152 contracts to fix post 118 with receiver 138. End surface 168 is engageable with collet 152 between an orientation such that surfaces 154, 164 are substantially aligned, and an orientation such that collet 152 is contractible to fix post 118 with receiver 138. End surface 168 includes a concave surface 170, disposed to abut collet 152 to drive collet 152 inward to contract collet 152.

Cavity 146, similar to cavity 46 as described herein, extends along a longitudinal axis FF and includes a transverse passageway 172 relative to longitudinal passageway 148, as shown in FIG. 10. Cavity 146 includes a top loading cavity configured for disposal of rod 116. In some embodiments, surface 144 includes a threaded portion configured for engagement with threads of a setscrew 145, as shown in FIG. 11. Cavity 146 includes a substantially U-shaped cross section. A saddle 176, similar to saddle 76 as described herein, is disposed with cavity 146, as shown in FIG. 10. A pin 190, similar to pin 90 as described herein, is configured for disposal with saddle 176.

Figure 13:
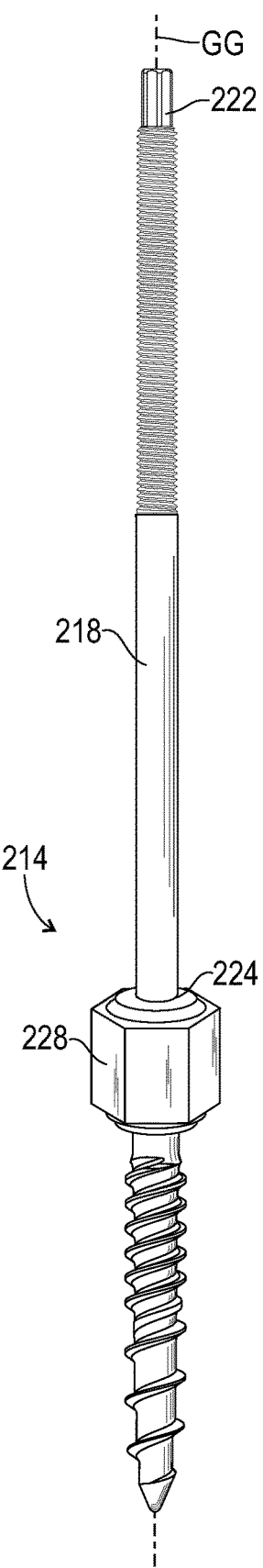
FIG. 13 is a perspective view of components shown in FIG. 12.

In one embodiment, as shown in FIGS. 12-23, spinal implant system 10, similar to the systems and methods described herein, includes a spinal construct 211, similar to spinal construct 11 described herein. Spinal construct 211 includes a connector 212, similar to connector 12 described herein, and a bone fastener, for example, a multi-axial screw 214, similar to screw 14 described herein. Connector 212 is configured for dorsal height adjustment relative to a post 218 of screw 214, as shown in FIG. 12 and described herein. Screw 214 extends along a longitudinal axis GG, as shown in FIG. 13. Screw 214 includes post 218, similar to post 18, connected to a threaded shaft 220, similar to shaft 20. Post 218 includes an end 222 and an end 224, as shown in FIG. 13. End 222 engages with one or more instruments, for example, a driver (not shown) to rotate screw 214. End 222 includes threads.

Figure 15:
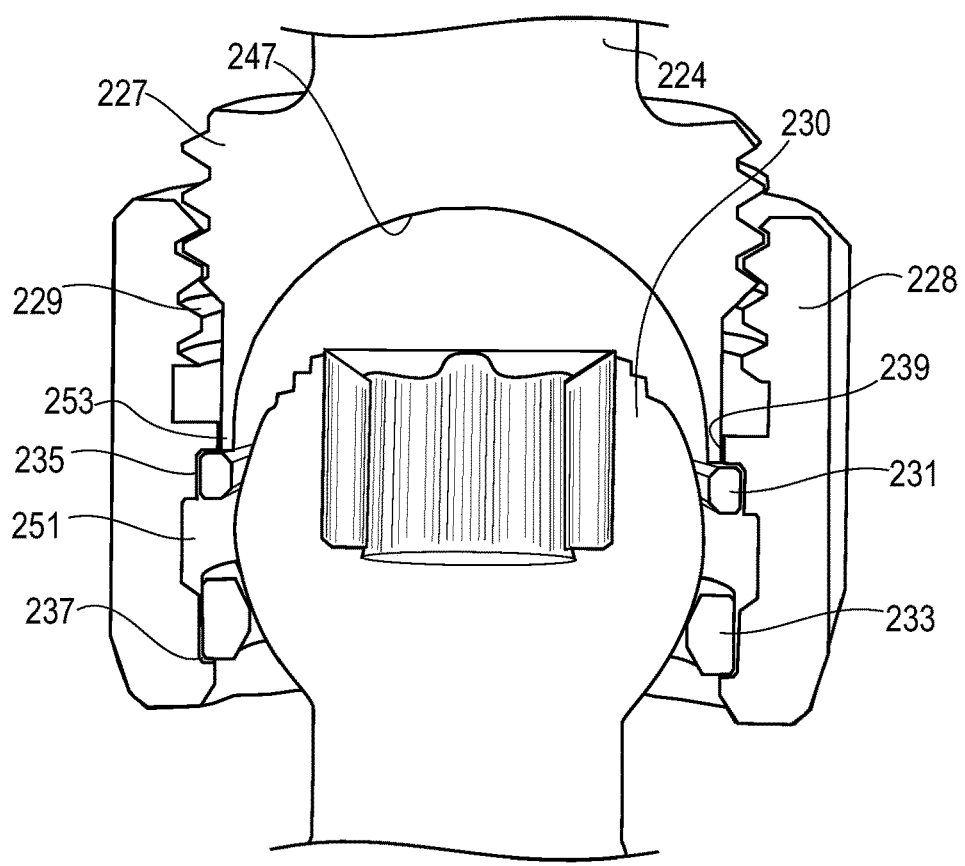
FIG. 15 is an enlarged cross section view of components shown in FIG. 12.

End 224 includes a threaded portion 227 and a base 228, as shown in FIG. 15. Base 228 is configured for engagement with a head 230 of shaft 220. Portion 227 and base 228 are configured for modular and/or pop-on connection with head 230. In some embodiments, portion 227 and base 228 manually engage head 230 in a snap-fit and/or pop-fit engagement. An inner threaded surface 229 of base 228 is configured for threaded engagement with portion 227. Portion 227 at an end 253 is welded onto an inner surface 239 of base 228 above a resilient member, for example, a ring 231, as shown in FIG. 15. In some embodiments, portion 227 is spot welded onto surface 239. In some embodiments, a breaking torque of 2-5 Nm is applied to post 218 via rotation and/or translation of post 218 such that portion 227 can rotationally translate within base 228.

Figures 16, 17:
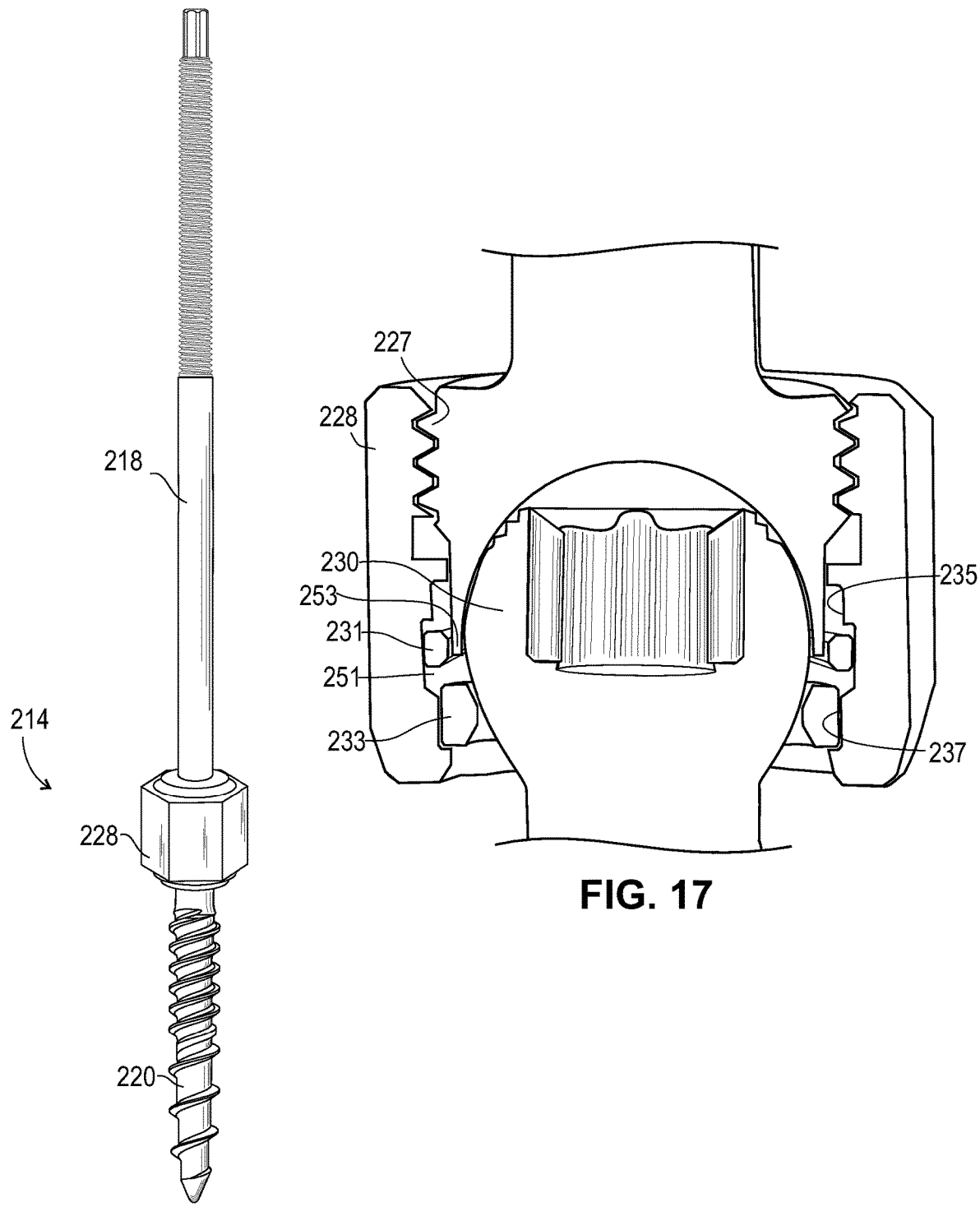
FIG. 16 is a perspective view of components shown in FIG. 13.
FIG. 17 is an enlarged cross section view of components shown in FIG. 12.

Ring 231 engages with head 230 and is configured for disposal with one or more grooves, for example, upper groove 235 and expansion groove 251 that are defined from surface 239 of base 228, as show in FIGS. 15 and 17, as described herein. Ring 231 includes a circumference that defines an opening, for example, a gap. A resilient member, for example, a ring 233 engages with head 230 and is configured for engagement with a lower groove 237 defined from surface 239 and groove 251, as described herein. Ring 233 includes a circumference that defines an opening, for example, a gap. Translation of head 230 within base 228 translates ring 233 from groove 237 into groove 251. Rotation and disposal of portion 227 within base 228 translates ring 231 from groove 235 into groove 251, and ring 233 is translated from groove 251 into groove 237 as portion 227 contacts head 230, as shown in FIGS. 15 and 17. Ring 231 fixes portion 227 with head 230, and ring 233 fixes head 230 with base 228, as shown in FIG. 17.

Shaft 220, similar to shaft 20 described herein, engages with vertebral tissue. Shaft 220 extends from an end 232 to an end 234, as show in FIG. 14. End 232 includes head 230 and end 234 includes a threaded portion 236. Head 230 includes a surface 241 that includes planar surfaces, for example, flats 243 and arcuate surfaces 245 for engagement with an arcuate surface 247 of end 224, rings 231, 233, and/or base 228, as shown in FIGS. 14 and 15.

Figure 14:
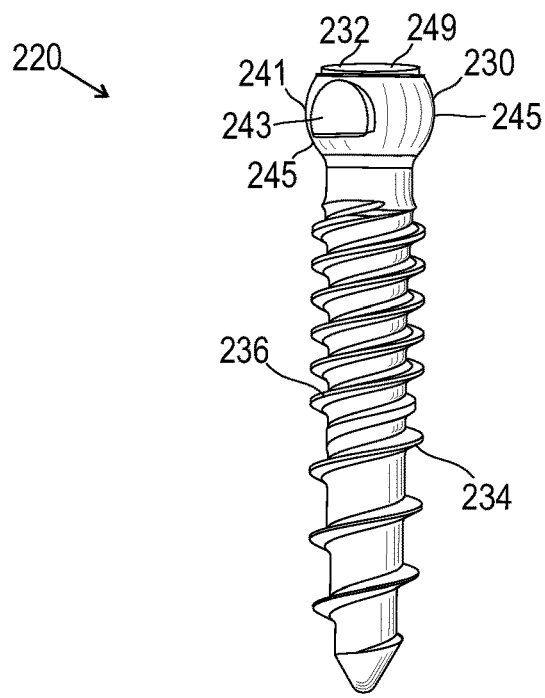
FIG. 14 is a perspective view of components shown in FIG. 12.

Head 230 includes a tool engaging portion 249 to engage a surgical tool or instrument, as shown in FIG. 14. In some embodiments, portion 249 includes a hexagonal cross-section to facilitate engagement with a surgical tool or instrument, as described herein. In some embodiments, portion 249 may have alternative cross-sections, for example, rectangular, polygonal, hexalobe, oval, or irregular.

Connector 212 is configured to facilitate procedures performed on a body and/or vertebrae of a patient on a selected plane for example, a sagittal plane. Connector 212 is engageable with screw 214 and a spinal rod 216, as shown in FIG. 12. Connector 212 includes a receiver 238, similar to receiver 38 described herein, as shown in FIG. 19. Receiver 238 is configured for dorsal height adjustment relative to post 218. An inner surface 240 of receiver 238 defines a cavity 242, similar to cavity 42 as described herein, for disposal of screw 214 and an inner surface 244 of receiver 238 defines an open cavity 246 for disposal of rod 216. Cavity 242 extends along a longitudinal axis HH and includes a longitudinal passageway 248.

A collet (not shown), similar to collet 52 as described herein, and a nut 262 similar to nut 62 as described herein, are configured for disposal with cavity 242 and for engagement to fix post 218 with receiver 238, as described herein. Alternatively, the collet may be similar to collet 152 and nut 262 may be similar to nut 162.

Cavity 246, similar to cavity 46 as described herein, extends along a longitudinal axis II and includes a transverse passageway 272 relative to longitudinal passageway 248, as shown in FIG. 19. Cavity 246 includes a top loading cavity configured for disposal of rod 216. In some embodiments, surface 244 includes a threaded portion configured for engagement with threads of a setscrew 245, as shown in FIG. 19. Cavity 246 includes a substantially U-shaped cross section. In some embodiments, a saddle (not shown) is disposed with cavity 246 and engages with rod 216.

To assemble screw 214 with connector 212, head 230 of shaft 220 engages with base 228, as shown in FIG. 13. A breaking torque of 2-5 Nm is applied to post 218 via rotation and translation of post 218 such that portion 227 can translate within base 228 to connect/fix portion 227 and base 228 with head 230. Base 228 and portion 227 are connected/fixed to head 230 when threads of portion 227 are entirely disposed within base 228. In some embodiments, multi-axial rotation of screw 214 can occur when threads of portion 227 are completely disposed within base 228. In some embodiments, a portion of the threads of portion 227 are exposed to display that post 218 has not been connected/fixed with base 228. In some embodiments, a surgical instrument, for example, a counter torque driver (not shown) is employed to prevent base 228 from rotating on shaft 220.

Post 218 is disposed with cavity 242 of receiver 238 and is translated in a direction, as shown by arrow B in FIG. 18, toward base 228 and shaft 220. Rod 216 is disposed with cavity 246 to secure rod 216 with receiver 238, as shown in FIG. 19. Rod 216 is provisionally secured with set screw 245. Rod 216 is reduced along post 218, as shown in FIG. 20. In some embodiments, rod 216 reduction can be stopped at any location relative to post 218. Base 228 and portion 227 create a multi-axial joint with head 230 and the joint is fixed/locked via a surgical instrument, for example, a torque limit handle (not shown). In some embodiments, a surgical instrument, for example, a counter torque driver (not shown) and/or crow-foot device (not shown) is implemented to prevent base 228 from rotating relative to head 230 of shaft 220 during joint fixation. Nut 262 and setscrew 245 are tightened to fix rod 216 with cavity 246, as shown in FIG. 23. In some embodiments, a user removes a portion of post 218 from base 228 and head 230, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
a bone fastener including a post and a shaft portion engageable with vertebral tissue; the post being movable in one or more axes relative to the shaft portion;
a receiver defining a first cavity configured for disposal of the bone fastener and a second open cavity configured for disposal of a spinal rod;
a band disposable in the first cavity, the band being contractible and defining an inner surface that is directly engageable with the post, the band extending between a first end and a second end, the first end including an angled surface and the second end including an angled surface, the band including a sidewall defining an axial gap that extends from the first end to the second end; and
a nut including an inner surface being slidably engageable over the post and an end surface engageable with the angled surface of the first end of the band such that the band contracts to engage the post.

2. A spinal construct as recited in claim 1, wherein the end surface is engageable with the band between a first orientation such that the inner surfaces are substantially aligned and a second orientation such that the band is contractible to fix the post with the receiver.

3. A spinal construct as recited in claim 1, wherein the post includes a joint connected to the shaft portion such that the post is movable relative to the shaft portion.

4. A spinal construct as recited in claim 1 wherein the receiver is configured for dorsal height adjustment relative to the post.

5. A spinal construct as recited in claim 1, wherein the axial gap expands and contracts.

6. A spinal construct as recited in claim 1, wherein the band includes a collet.

7. A spinal construct as recited in claim 6, wherein an inner surface of the receiver defines the first cavity, the first cavity including a longitudinal passageway, the inner surface defining threads that facilitate inward flex of the collet.

8. A spinal construct as recited in claim 1, wherein the end surface of the nut includes a concave surface disposed to abut the angled surface of the first end of the band.

9. A spinal construct as recited in claim 1, wherein the band includes an outer surface that defines one or more flats configured for engagement with one or more flats of the receiver.

10. A spinal implant as recited in claim 9, wherein engagement of the one or more flats is configured to prevent rotation of the band.

11. A spinal construct as recited in claim 1, wherein the bone fastener includes a multi-planar adjusting screw.

12. A spinal construct as recited in claim 1, wherein the second open cavity includes a top loading cavity.

13. A spinal construct as recited in claim 1, wherein an inner surface of the receiver defines the second cavity, the second cavity including a transverse passageway relative to the longitudinal passageway.

14. A spinal construct comprising:
a multi-planar adjusting screw including a post and a shaft portion engageable with vertebral tissue;
a receiver including an inner surface that defines a first cavity configured for disposal of the multiplanar adjusting screw and a top loading cavity configured for disposal of a spinal rod;
a collet disposable in the first cavity, the collet defining an inner surface that is directly engageable with the post, the collet extending between a first end and a second end, the first end including an angled surface and the second end including an angled surface, the collet including a sidewall defining an axial gap that extends from the first end to the second end; and
a nut including an inner surface being engageable with the post and an end surface engageable with the angled surface of the first end of the collet between a first orientation such that the inner surfaces are substantially aligned and a second orientation such that the collet is movable to fix the post with the receiver, the angled surface of the second end being engageable with the inner surface of the receiver.

15. A spinal construct as recited in claim 14, wherein the post includes a joint connected to the shaft portion such that the post is movable relative to the shaft.

16. A spinal construct as recited in claim 14, wherein the first cavity includes a longitudinal passageway, the inner surface including threads.

17. A spinal construct as recited in claim 14, wherein the end surface of the nut includes a concave edge.

18. A spinal implant system comprising:
an adjustable bone fastener including a post connected with a threaded shaft via a joint;
a receiver defining a first cavity configured for disposal of the bone fastener and a second open cavity;
a band disposable in the first cavity, the band being contractible and defining an inner surface that is directly engageable with the post, the band extending between a first end and a second end, the first end including an angled surface and the second end including an angled surface, the band including a sidewall defining an axial gap that extends from the first end to the second end;
a nut including an inner surface being engageable with the post and an end surface engageable with the angled surface of the first end of the band such that the band contracts to fix the post with the receiver; and
a spinal rod disposable in the second cavity.

19. A spinal implant system as recited in claim 18, wherein the post is movable along one or more axes for dorsal, sagittal or medial/lateral adjustment.

\* \* \* \* \*